(12) United States Patent
Ren et al.

(10) Patent No.: US 11,580,673 B1
(45) Date of Patent: Feb. 14, 2023

(54) METHODS, SYSTEMS, AND COMPUTER READABLE MEDIA FOR MASK EMBEDDING FOR REALISTIC HIGH-RESOLUTION IMAGE SYNTHESIS

(71) Applicant: Duke University, Durham, NC (US)

(72) Inventors: Yinhao Ren, Durham, NC (US); Joseph Yuan-Chieh Lo, Chapel Hill, NC (US)

(73) Assignee: Duke University, Durham, NC (US)

( * ) Notice: Subject to any disclaimer, the term of this patent is extended or adjusted under 35 U.S.C. 154(b) by 94 days.

(21) Appl. No.: 16/893,053

(22) Filed: Jun. 4, 2020

Related U.S. Application Data

(60) Provisional application No. 62/856,938, filed on Jun. 4, 2019.

(51) Int. Cl.
*G06T 11/00* (2006.01)
*G16H 30/40* (2018.01)
*G06N 3/08* (2023.01)
*G06N 3/04* (2023.01)
*G16H 50/20* (2018.01)

(52) U.S. Cl.
CPC ............ *G06T 11/00* (2013.01); *G06N 3/0454* (2013.01); *G06N 3/088* (2013.01); *G16H 30/40* (2018.01); *G16H 50/20* (2018.01); *G06T 2210/41* (2013.01)

(58) Field of Classification Search
CPC ..... G06T 11/00; G06T 2210/41; G16H 50/20; G16H 30/40; G06N 3/0454; G06N 3/088
See application file for complete search history.

(56) References Cited

U.S. PATENT DOCUMENTS

| | | | | |
|---|---|---|---|---|
| 10,049,308 B1* | 8/2018 | Dhua | .................. | G06K 9/6256 |
| 10,317,499 B2* | 6/2019 | Chen | .................... | A61B 5/0044 |
| 10,424,087 B2* | 9/2019 | Risser | ..................... | G06T 11/00 |
| 10,540,757 B1* | 1/2020 | Bouhnik | .............. | G06T 3/4084 |
| 10,540,798 B1* | 1/2020 | Walters | ................ | G06T 11/001 |
| 10,803,646 B1* | 10/2020 | Bogan, III | ........... | G06V 40/174 |
| 10,810,435 B2* | 10/2020 | Lee | ......................... | G06V 20/70 |
| 10,872,399 B2* | 12/2020 | Li | .......................... | G06N 3/088 |
| 11,024,060 B1* | 6/2021 | Ma | ....................... | G06V 40/103 |

(Continued)

OTHER PUBLICATIONS

Antipov et al., "Face aging with conditional generative adversarial networks." 2017 IEEE International Conference on Image Processing (ICIP), pp. 2089-2093 (Sep. 2017).

(Continued)

*Primary Examiner* — Charles L Beard
(74) *Attorney, Agent, or Firm* — Jenkins, Wilson, Taylor & Hunt, P.A.

(57) ABSTRACT

The subject matter described herein includes methods, systems, and computer readable media for mask embedding for realistic high-resolution image synthesis. According to one method for mask embedding for realistic high-resolution image synthesis includes receiving, as input, a mask embedding vector and a latent features vector, wherein the mask embedding vector acts as a semantic constraint; generating, using a trained image synthesis algorithm and the input, a realistic image, wherein the realistic image is constrained by the mask embedding vector; and outputting, by the trained image synthesis algorithm, the realistic image to a display or a storage device.

17 Claims, 10 Drawing Sheets

(56) References Cited

U.S. PATENT DOCUMENTS

| | | | |
|---|---|---|---|
| 11,030,782 B2* | 6/2021 | Ayush | G06N 3/0454 |
| 11,055,828 B2* | 7/2021 | Long | G06V 10/30 |
| 11,126,895 B2* | 9/2021 | Anirudh | G06V 10/764 |
| 11,127,225 B1* | 9/2021 | Kowalski | G06T 17/00 |
| 11,158,055 B2* | 10/2021 | Lin | G06N 3/082 |
| 11,158,403 B1* | 10/2021 | Sapiro | G16H 40/60 |
| 11,169,263 B2* | 11/2021 | Tang | G06N 3/088 |
| 11,189,028 B1* | 11/2021 | Kearney | G06N 3/08 |
| 2017/0193400 A1* | 7/2017 | Bhaskar | G06N 3/0454 |
| 2018/0247201 A1* | 8/2018 | Liu | G06N 3/0454 |
| 2019/0057521 A1* | 2/2019 | Teixeira | G06K 9/6274 |
| 2019/0066281 A1* | 2/2019 | Zheng | G06T 5/006 |
| 2019/0114748 A1* | 4/2019 | Lin | G06T 5/005 |
| 2019/0122072 A1* | 4/2019 | Cheri | G06V 10/764 |
| 2019/0147320 A1* | 5/2019 | Mattyus | G06V 20/182 382/155 |
| 2019/0228508 A1* | 7/2019 | Price | G06T 7/344 |
| 2019/0251401 A1* | 8/2019 | Shechtman | G06V 30/19173 |
| 2019/0295223 A1* | 9/2019 | Shen | G06T 7/0002 |
| 2019/0295302 A1* | 9/2019 | Fu | G06N 3/088 |
| 2019/0347831 A1* | 11/2019 | Vishnu Vardhan | G06T 11/00 |
| 2019/0369191 A1* | 12/2019 | Gong | A61B 5/055 |
| 2019/0370969 A1* | 12/2019 | Alexander | G06N 3/0454 |
| 2020/0005511 A1* | 1/2020 | Kavidayal | G06N 3/088 |
| 2020/0013196 A1* | 1/2020 | Vishnu Vardhan | G06T 11/001 |
| 2020/0026416 A1* | 1/2020 | Bala | G06F 3/04845 |
| 2020/0074271 A1* | 3/2020 | Liang | G06N 3/0454 |
| 2020/0074707 A1* | 3/2020 | Lee | G06K 9/6262 |
| 2020/0090350 A1* | 3/2020 | Cho | G06T 7/136 |
| 2020/0134375 A1* | 4/2020 | Zhan | G06V 10/26 |
| 2020/0151938 A1* | 5/2020 | Shechtman | G06N 3/0454 |
| 2020/0210770 A1* | 7/2020 | Bala | G06K 9/00 |
| 2020/0242774 A1* | 7/2020 | Park | G06T 11/001 |
| 2020/0242800 A1* | 7/2020 | Chen | G06T 7/73 |
| 2020/0302176 A1* | 9/2020 | Yang | G06V 10/774 |
| 2020/0311932 A1* | 10/2020 | Hooper | G06N 3/088 |
| 2020/0320777 A1* | 10/2020 | Meshry | G06T 19/20 |
| 2020/0364860 A1* | 11/2020 | Kearney | G06N 3/0454 |
| 2020/0372301 A1* | 11/2020 | Kearney | G16H 20/40 |
| 2020/0380652 A1* | 12/2020 | Olaleye | G06V 20/20 |
| 2020/0387829 A1* | 12/2020 | Kearney | G06T 5/002 |
| 2020/0394459 A1* | 12/2020 | Xu | G06N 3/0472 |
| 2020/0405242 A1* | 12/2020 | Kearney | A61B 6/5217 |
| 2020/0410649 A1* | 12/2020 | Kearney | G06N 3/0454 |
| 2020/0411167 A1* | 12/2020 | Kearney | G06N 3/0445 |
| 2020/0411201 A1* | 12/2020 | Kearney | G06N 3/08 |
| 2021/0042558 A1* | 2/2021 | Choi | G06T 11/60 |
| 2021/0073630 A1* | 3/2021 | Zhang | G06N 3/0454 |
| 2021/0089845 A1* | 3/2021 | Galeev | G06K 9/6273 |
| 2021/0097678 A1* | 4/2021 | Dutta | G06N 3/0454 |
| 2021/0098127 A1* | 4/2021 | Kalafut | G16H 30/40 |
| 2021/0118099 A1* | 4/2021 | Kearney | G06N 3/08 |
| 2021/0118129 A1* | 4/2021 | Kearney | G06N 3/088 |
| 2021/0118132 A1* | 4/2021 | Kearney | G06N 3/0472 |
| 2021/0118149 A1* | 4/2021 | Sollami | G06V 40/103 |
| 2021/0142177 A1* | 5/2021 | Mallya | G06N 3/084 |
| 2021/0150357 A1* | 5/2021 | Karras | G06N 3/088 |
| 2021/0150369 A1* | 5/2021 | Karras | G06V 10/454 |
| 2021/0158430 A1* | 5/2021 | Buibas | G06V 10/255 |
| 2021/0178274 A1* | 6/2021 | St-Pierre | G06K 9/627 |
| 2021/0201499 A1* | 7/2021 | Qin | G06N 3/0454 |
| 2021/0217145 A1* | 7/2021 | El-Khamy | G06T 5/50 |
| 2021/0232803 A1* | 7/2021 | Fu | G06T 11/00 |
| 2021/0241500 A1* | 8/2021 | Chen | G06N 20/00 |
| 2021/0264207 A1* | 8/2021 | Smith | G06V 10/82 |
| 2021/0275918 A1* | 9/2021 | Devaranjan | G06T 17/00 |
| 2021/0287780 A1* | 9/2021 | Korani | G16H 30/20 |
| 2021/0303927 A1* | 9/2021 | Li | G06K 9/6257 |
| 2021/0327028 A1* | 10/2021 | Machii | G06N 3/0472 |
| 2021/0334935 A1* | 10/2021 | Grigoriev | G06N 3/08 |
| 2021/0342984 A1* | 11/2021 | Lin | G06T 5/50 |
| 2021/0343063 A1* | 11/2021 | Garbin | G06K 9/6247 |
| 2021/0353393 A1* | 11/2021 | Kearney | G16H 30/40 |
| 2021/0357688 A1* | 11/2021 | Kearney | G06V 10/82 |
| 2021/0358123 A1* | 11/2021 | Kearney | G16H 30/40 |
| 2021/0358197 A1* | 11/2021 | Shysheya | G06T 15/04 |
| 2021/0358604 A1* | 11/2021 | Kearney | G06N 3/0445 |
| 2021/0365736 A1* | 11/2021 | Kearney | A61B 6/563 |
| 2021/0366173 A1* | 11/2021 | Sinha | G06V 40/171 |
| 2021/0374551 A1* | 12/2021 | Vijil | G16C 20/50 |
| 2021/0406516 A1* | 12/2021 | Chen | G06V 10/7715 |
| 2022/0004803 A1* | 1/2022 | Li | G06N 3/04 |
| 2022/0012815 A1* | 1/2022 | Kearney | G06N 3/0454 |
| 2022/0028139 A1* | 1/2022 | Mitra | G06V 10/422 |
| 2022/0044365 A1* | 2/2022 | Zhang | G06T 3/40 |
| 2022/0044366 A1* | 2/2022 | Zhang | G06T 7/12 |
| 2022/0101577 A1* | 3/2022 | Chakrabarty | G06T 11/60 |
| 2022/0108417 A1* | 4/2022 | Liu | G06T 11/001 |
| 2022/0120664 A1* | 4/2022 | Rognin | G06N 3/08 |
| 2022/0147768 A1* | 5/2022 | Thermos | G06T 7/0012 |
| 2022/0148242 A1* | 5/2022 | Russell | G06T 11/60 |
| 2022/0164947 A1* | 5/2022 | Yu | G06T 7/11 |
| 2022/0215266 A1* | 7/2022 | Venkataraman | G06K 9/6256 |
| 2022/0222872 A1* | 7/2022 | Ghosh | G06T 11/40 |

OTHER PUBLICATIONS

Antoniou et al., "Data augmentation generative adversarial networks," pp. 1-14 (2018).
Arjovksy et al., "Wasserstein generative adversarial networks." In: Proceedings of the 34th International Conference on Machine Learning. vol. 70, pp. 214-223 (2017).
Bayramoglu et al., "Towards virtual h&e staining of hyperspectral lung histology images using conditional generative adversarial networks." In 2017 IEEE International Conference 15 on Computer Vision Workshops (ICCVW), pp. 64-71 (Oct. 2017).
Che et al., "Mode regularized generative adversarial networks," pp. 1-13, CoRR abs/1612.02136 (2016).
Chen et al., "Matching Thermal to Visible Face Images Using a Semantic-Guided Generative Adversarial Network," 8 pages, arXiv e-prints, arXiv: 1903.00963 (Mar. 2019).
Chen et al., "Photographic image synthesis with cascaded refinement networks." IEEE International Conference on Computer Vision, ICCV 2017, Venice, Italy, Oct. 22-29, 2017, pp. 1520-1529 (2017).
Costa et al., "End-to-end adversarial retinal image synthesis." IEEE Transactions on Medical Imaging vol. 37(3), pp. 781-791 (Mar. 2018).
Curto et al., "High-resolution deep convolutional generative adversarial networks," pp. 1-9, arxiv:1711.06491 (2017).
Dar et al., "Image synthesis in multi-contrast MRI with conditional generative adversarial networks," IEEE Transactions on Medical Imaging, vol. 38, No. 10, pp. 2375-2388 (2019).
Gauthier, "Conditional generative adversarial nets for convolutional face generation," pp. 1-9 (2015).
Goodfellow et al., "Generative adversarial nets." In: Advances in Neural Information Processing Systems vol. 27, pp. 2672-2680 (2014).
Gulrajani et al., "Improved training of Wasserstein gans." In: Advances in Neural Information Processing Systems, pp. 5767-5777 (2017).
Han et al., "Gan-based synthetic brain MR image generation," In: 2018 IEEE 15th International Symposium on Biomedical Imaging (ISBI 2018), pp. 734-738 (Apr. 2018).
Heusel et al., "Gans trained by a two time-scale update rule converge to a nash equilibrium," pp. 1-38, CoRR abs/1706.08500 (2017).
Isola et al., "Image-to-image translation with conditional adversarial networks," In: The IEEE Conference on Computer Vision and Pattern Recognition (CVPR), 17 pages (Jul. 2017).
Rabin et al., "Wasserstein Barycenter and its Application to Texture Mixing." SSVM'11, pp. 435-446, Israel, 2011. Springer (2011).
Karras et al., "A style-based generator architecture for generative adversarial networks," pp. 1-12, CoRR abs/1812.04948 (2018).
Karras et al., "Progressive growing of GANs for improved quality, stability, and variation," pp. 1-26, CoRR abs/1710.10196 (2017).
King, "Dlib-ml: A machine learning toolkit." Journal of Machine Learning Research, vol. 10, pp. 1755-1758 (2009).

(56) References Cited

OTHER PUBLICATIONS

Korkinof et al., "High-resolution mammogram synthesis using progressive generative adversarial networks," pp. 1-19, CoRR abs/1807.03401 (2018).

Liu et al., "Deep learning face attributes in the wild," Proceedings of International Conference on Computer Vision (ICCV), 11 pages (Dec. 2015).

Liu et al., "Semantic image synthesis via conditional cycle-generative adversarial networks." 2018 24th International Conference on Pattern Recognition (ICPR), pp. 988-993 (Aug. 2018).

Mirza, "Conditional Generative Adversarial Nets," pp. 1-7, CoRR, abs/1411.1784 (2014).

Moradi et al., "Chest x-ray generation and data augmentation for cardiovascular abnormality classification." SPIE Medical Imaging, 2018, Houston, Texas, United States, 8 pages (Mar. 2018).

Nie et al., "Medical image synthesis with context-aware generative adversarial networks." In: Medical Image Computing and Computer-Assisted Intervention MICCAI 2017. pp. 417-425. Springer International Publishing, Cham (2017).

Nie et al., "Medical image synthesis with deep convolutional adversarial networks." IEEE Transactions on Biomedical Engineering 65(12), pp. 2720-2730 (Dec. 2018).

Rezaei et al., "A conditional adversarial network for semantic segmentation of brain tumor." Brainlesion: Glioma, Multiple Sclerosis, Stroke and Traumatic Brain Injuries, pp. 241-252, Springer International Publishing, Cham (2018).

Ronneberger et al., "U-net: Convolutional networks for biomedical image segmentation," pp. 1-8, CoRR abs/1505.04597 (2015).

Salimans et al., "Improved techniques for training gans." In: Advances in Neural Information Processing Systems vol. 29, pp. 2234-2242 (2016).

Shaham et al., "SinGAN: Learning a Generative Model from a Single Natural Image," 11 pages, arXiv e-prints, p. arXiv:1905.01164 (May 2019).

Wang et al., "Facial expression synthesis by u-net conditional generative adversarial networks." Proceedings of the 2018 ACM on International Conference on Multimedia Retrieval, ICMR '18, pp. 283-290, New York, NY, USA, ACM (2018).

Wang et al., "High-resolution image synthesis and semantic manipulation with conditional GANs," Proceedings of the IEEE Conference on Computer Vision and Pattern Recognition, pp. 1-14 (2018).

Yi et al., "Generative adversarial network in medical imaging: A review," pp. 1-24, CoRR abs/1809.07294 (2018).

Yildirim et al., "Disentangling Multiple Conditional Inputs in GANs," arXiv e-prints, 5 pages, arXiv:1806.07819 (Jun. 2018).

Zhang et al., "StackGAN: Text to photo-realistic image synthesis with stacked generative adversarial networks," 14 pages, ICCV (2017).

Zhao et al., "Synthesizing retinal and neuronal images with generative adversarial nets." Medical Image Analysis, vol. 49, pp. 14-26 (2018).

\* cited by examiner

| Configurations | 512 | 256 | 128 | 64 | 32 | 16 | Avg |
|---|---|---|---|---|---|---|---|
| Real | 10.82 | 9.98 | 10.14 | 9.75 | 9.83 | 7.52 | 9.67 |
| Pix2Pix | 67.74 | 27.72 | 25.08 | 20.46 | 19.05 | 151.78 | 65.52 |
| Without Embedding | 58.20 | 27.77 | 22.19 | 18.25 | 17.58 | 70.49 | 35.75 |
| With Embedding | 43.74 | 22.46 | 17.48 | 14.83 | 13.65 | 37.57 | 24.96 |

METHODS, SYSTEMS, AND COMPUTER READABLE MEDIA FOR MASK EMBEDDING FOR REALISTIC HIGH-RESOLUTION IMAGE SYNTHESIS

CROSS REFERENCE TO RELATED APPLICATIONS

This application claims the benefit of U.S. Provisional Patent Application Ser. No. 62/856,938, filed Jun. 4, 2019, the disclosure of which is incorporated herein by reference in its entirety.

TECHNICAL FIELD

The subject matter described herein relates generally to machine learning algorithms. More particularly, the subject matter described herein includes methods, systems, and computer readable media for mask embedding for realistic high-resolution image synthesis.

BACKGROUND

Generative adversarial networks (GANs) have applications in natural image synthesis and show promise for generating synthetic medical images. In some scenarios, the ability to perform controlled image synthesis using masks or related information may be useful. However, mask-guided image synthesis is challenging since it typically requires complicated models to create highly realistic images. Furthermore, existing mask-guided image generation approaches suffer from modal collapse, resulting in the lack of diversity in the images.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

The subject matter described herein includes methods, systems, and computer readable media utilizing mask embedding for realistic high-resolution image synthesis. According to one method for realistic high-resolution image synthesis includes receiving, as input, a mask embedding vector and a latent features vector (e.g., the mask embedding vector may be coupled to the latent features vector), wherein the mask embedding vector acts as a semantic constraint; generating, using a trained image synthesis algorithm and the input, a realistic image, wherein the realistic image is constrained by the mask embedding vector; and outputting, by the trained image synthesis algorithm, the realistic image to a display or to a storage device.

A system for realistic high-resolution image synthesis is also disclosed. In some embodiments, the system includes a computing platform including at least one processor and memory. In some embodiments, the computing platform is configured for: receiving, as input, a mask embedding vector and a latent features vector, wherein the mask embedding vector acts as a semantic constraint; generating, using a trained image synthesis algorithm and the input, a realistic image, wherein the realistic image is constrained by the mask embedding vector; and outputting, by the trained image synthesis algorithm, the realistic image to a display or a storage device.

The subject matter described herein may be implemented in software in combination with hardware and/or firmware. For example, the subject matter described herein may be implemented in software executed by a processor (e.g., a hardware-based processor). In one example implementation, the subject matter described herein may be implemented using a non-transitory computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, such as field programmable gate arrays, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which:

FIG. 4 is a table containing sliced Wasserstein distance (SWD) values for different image synthesis systems at different configurations;

DETAILED DESCRIPTION

Figure 1:
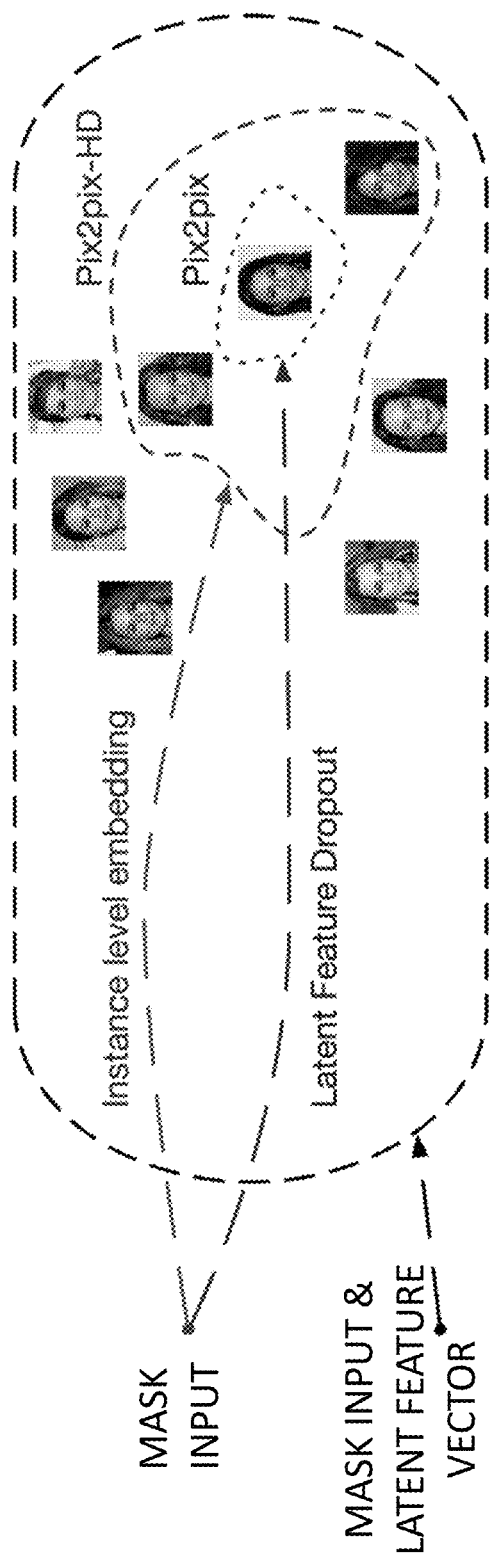
FIG. 1 illustrates how using mask input and a latent features vector at an initial projection layer allows an image synthesis model to utilize a larger subset of an entire domain space compared to other models.

The subject matter described herein relates, in part, systems, methods, and computer readable media for mask-guided image synthesis that involves encoding a mask input as an embedding vector and then injecting the embedding vector into a latent features vector input. A challenge in training an image translation or synthesis model with latent features vector input is producing latent features that are compatible with mask input (e.g., a mask constraint). In other words, an initial latent projection layer of machine learning based synthesis model could produce features that fall outside the manifold constrained by the semantic mask input in the latent space, resulting in using subsequent deconvolution layers to compensate for this inefficiency, and eventually leading to model capacity reduction.

In some embodiments, systems, methods, and computer readable media provided herein relates to an image synthesis model (e.g., an algorithm or process) that uses an additional constraint on initially projected features by injecting a mask embedding vector into a latent features vector. In such embodiments, the image synthesis model can perform a more efficient initial feature projection by producing latent features that are compatible with the mask input, thereby preserving or improving output image quality over other models.

By providing techniques, mechanisms, systems, and/or methods for using a mask embedding vector and a latent features vector, realistic high-resolution images may be generated with semantic control. For example, a conditional generative adversarial network (cGAN) or another system or algorithm may take as input, a semantic mask (e.g., an edge map showing a breast shape or position) and a latent features vector at an initial latent projection layer, and may use the input to generate a realistic high-resolution image (e.g., a mammogram). In another example, a cGAN or another system or algorithm may take as input, a semantic mask (e.g., an binary image represent facial features or facial expressions) and a latent features vector at an initial latent projection layer, and may use the input to generate a realistic high-resolution image of a human face.

As used herein, the term "node" refers to a physical computing platform including one or more processors and memory.

As used herein, the terms "function" or "module" refer to software in combination with hardware and/or firmware for implementing features described herein. In some embodiments, a module may include a field-programmable gate array (FPGA), an application-specific integrated circuit (ASIC), or a processor.

Articles "a" and "an" are used herein to refer to one or to more than one (i.e. at least one) of the grammatical object of the article. By way of example, "an element" means at least one element and can include more than one element.

As used herein, the term "and/or" when used in the context of a list of entities, refers to the entities being present singly or in any and every possible combination and subcombination. Thus, for example, the phrase "A, B, C, and/or D" includes A, B, C, and D individually, but also includes any and all combinations and subcombinations of A, B, C, and D. It is further understood that for each instance wherein multiple possible options are listed for a given element (i.e., for all "Markush Groups" and similar listings of optional components for any element), in some embodiments the optional components can be present singly or in any combination or subcombination of the optional components. It is implicit in these forms of lists that each and every combination and subcombination is envisioned and that each such combination or subcombination has not been listed simply merely for convenience. Additionally, it is further understood that all recitations of "or" are to be interpreted as "and/or" unless the context clearly requires that listed components be considered only in the alternative (e.g., if the components would be mutually exclusive in a given context and/or could not be employed in combination with each other).

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of and "consisting of those certain elements. As used herein, "and/or" refers to and encompasses any and all possible combinations of one or more of the associated listed items, as well as the lack of combinations where interpreted in the alternative ("or"). As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising." Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

Introduction

The rapid development of generative models especially on training methodology [1, 9] and architecture [10], has led to the significant improvement of resolution and quality of the output images. In the image editing scenario, semantic control of the generated images (such as object category and shape) is highly desired. Many studies have explored cGANs [12, 4] using class labels (one-hot vectors) [4] and mask labels [8]. Producing highly stochastic outputs as well as capturing the full entropy of the conditional distributions are of a great challenge for current cGANs.

Many existing approaches with semantic mask inputs focus on either applying the coarse to fine synthesis with a cascade of networks [21, 22, 23], or designing specific loss functions [1, 5] to increase the model stability for better image quality. Though advances have been made, it is still challenging to synthesize high-resolution images with local feature diversity using semantic masks as guidance.

Many cGANs may derive from a basic generator-discriminator architecture. By adding conditional information to both the generator and the discriminator, cGANs can control some characteristics of the generated images. The most straightforward way to incorporate class label information is to directly concatenate the label vector with the latent features vector in the generator and then to concatenate the conditional information with the latent features in the discriminator [12]. On the other hand, incorporating a pixel-level mask label requires a special design of the networks to preserve the fine-grained texture details while satisfying the mask constraint [8].

The subject matter described herein includes a novel approach for generating realistic high-resolution medical images with semantic control. In some embodiments, the novel approach may utilize a U-Net [16] style generator that takes both a latent features vector (e.g., a Gaussian noise vector) and a semantic mask (e.g., a binary or edge map) as input. In such embodiments, the generator may generate a mask embedding vector and then concatenate the mask embedding vector to a latent noise vector as input of a feature projection path. The mask is an image providing constraints. For example, the mask may be an edge map, a segmentation map, a gradient field, etc.

In some embodiments, the subject matter described herein may involve techniques, methods, systems, or devices that use mask embedding in semantic cGANs for realistic image synthesis. For example, an example image synthesis system may take both a mask and a random latent features vector as input and may use this input to generate highly stochastic images with fine-grained details. In this example, the highly stochastic images may be human faces and the mask may be data for representing human facial features and/or human facial expressions (e.g., frowns, smiles, etc.)

In some embodiments, an example image synthesis system or a related process may be usable for medical image synthesis. For example, an example image synthesis system may synthesize realistic high-resolution mammograms using a binary mask that indicates the breast shape. In this example, the image synthesis system may generate realistic high-resolution mammograms with semantic control.

Although one aspect of the subject matter described herein is to tackle the mask-guided medical image synthesis problem, our proposed approach can potentially be applied to a much wider range of tasks and can improve the quality of mask-guided natural image synthesis. For example, a facial image synthesis example is also discussed and explored herein.

General Considerations

Medical image synthesis is a well-motivated research topic. The ability to generate a large number of realistic looking medical phantoms greatly enables studies such as virtual clinical trials and data augmentation for computer aided diagnosis algorithms.

Recently multiple studies have been using GANs to synthesize medical images. Those methods can be grouped into unconditioned synthesis [6, 13] and conditioned synthesis [3, 15, 14]. There is also a detailed survey of medical image synthesis using GANs [18]. Note that mammogram synthesis using GANs has been proposed in [11], but their approach focuses on image realism and resolution in the unconditional setting, hence the shape or other morphological characteristics of their synthesized mammograms cannot be controlled.

Conditional GAN

Conditional GANs [24] achieve the control of generator output through coupling of a latent features vector and conditional inputs. Many studies [25, 26, 27, 28, 29, 30] applied cGAN using image attributes in vector form (such as labels) for controlled image synthesis. Pix2Pix [8] and Pix2Pix-HD [21] proposed to use semantic input directly in an encoder-decoder style structure for image-to-image translation. Some studies have applied input embedding to transform a higher dimensional attribute such as semantic mask into a more compact lower dimensional form. CCGAN [31] proposed to use sentence embedding that contains image characteristics as a feature for cycle GAN training. CCGAN [31] shows condensed text information can be merged with generator latent features as conditions for image synthesis. Yildirim et al. [32] uses binary mask embedding as part of conditional input to control the shape of generated garment images. However, their work indicates that a mask embedding vector is not sufficient for pixel-level mask constrained image synthesis and that the output shape of their proposed model does not always align with the mask input.

State-of-the-Art Pix2Pix Style Generator

Many works [3, 8, 21, 33, 31] have applied image translation models to map an image from one domain to another. However, a typical Pix2Pix setup does not perform well in terms of fine-grained texture details and feature diversity. The state of art Pix2Pix-HD model on the other hand uses a coarse-to-fine model architecture design with perceptual loss and multi-scale discriminators. The Pix2Pix-HD model uses additional loss terms to regularize the expanded model capacity, especially the concatenated refinement networks. Though the Pix2Pix-HD model has a mechanism of randomizing the textures through instance level feature embedding, diversity of local texture details still relies on the minor perturbations of instance label maps. To some extent this mechanism allows stochastic texture generation, however, the mapping of textures is coupled only with the shape perturbation of objects. In other words, this image translation model is still limited to a one-to-one mapping, and the image quality and diversity is rather low due to this limitation.

Progressive Growing of GAN

Progressive growing of GAN (pGAN) [9] is a training methodology that gradually adds convolution layers to the generator and discriminator to achieve better stability and faster convergence. This technique makes it possible to synthesize high-resolution images using a slightly modified DCGAN [34] generator and discriminator architecture. Several recent studies [35, 36, 11] have applied a progressive training strategy and achieved high-resolution of synthesized results in non-conditional settings. In our mask-guided image synthesis scenarios described herein, a progressive training strategy is applied for generating high-resolution outputs.

Architecture

One challenge explored in the subject matter described herein is how to train an image translation model that uses latent features vector input to produce latent features that are compatible with an inputted mask constraint. For example, without such a model, an initial latent projection layer may produce features that fall outside the manifold constrained by a semantic mask input in the latent space. In this example, subsequent deconvolution layers may be required to compensate for this inefficiency, and eventually leading to model capacity reduction.

One approach for producing latent features that are compatible with an inputted mask constraint involves utilizes an additional constraint on initially projected features by injecting (e.g., concatenating) mask input (e.g., a mask embedding vector) into a latent features vector as input. By utilizing mask input and a latent features vector, a more efficient initial feature projection is performed that produces latent features compatible with the mask input, thereby preserving output image quality.

Mask Embedding in Generator

In some image translation models, to control the shape of generator output, a mask is typically used as the only input in an encoder-decoder style generator to enforce a pixel-level constraint. The fundamental principle of such image translation models is to build a translation of G(v)→{r} where one-to-one translations are established give input v. With a mechanism such as drop-out or noise overlaid to input v, the one-to-more relation R: {r1, r2 ... rm} becomes theoretically possible in ideal cases. However, limited by the convolution operations and choice of objective function, Pix2Pix reported that overlaid noise is often ignored by the model. Model output typically depends heavily on the semantic mask input and drop-out so that the diversity of high frequency texture patterns is limited. In other words, given a sub optimal image-to-image translation network G' the sampling scheme in practice becomes G' (v, z)→{r1, r2 ... rn} where n<<m. The mapped sample space thus becomes sparse.

FIG. 1 illustrates how using mask input and a latent features vector at an initial projection layer allows an image synthesis model to utilize a larger subset of an entire domain space compared to other models. As illustrated in FIG. 1, different strategies (e.g., Pix2Pix, Pix2Pix-HD, and our proposed mask embedding approach) may utilize different subsets of an entire domain space depending on input. FIG. 1 further illustrates that utilizing mask input and a latent features vector yields greater image generator performance (in terms of diversity, resolution, and realism) than Pix2Pix and Pix2Pix-HD.

Formulation

This section provides exemplary, non-limiting reasoning for an image synthesis approach described herein. For example, we can regard having both mask constraint and local fine-grained texture details at the same time as a space sampling problem, under the condition that the up-sampling is mostly conducted with convolution layers. In this example, mask input does not identify an image in the real image dataset, but instead relates to a cluster of real images. Hence, masks gathered from a dataset can define a partition of real image manifolds.

Figure 2:
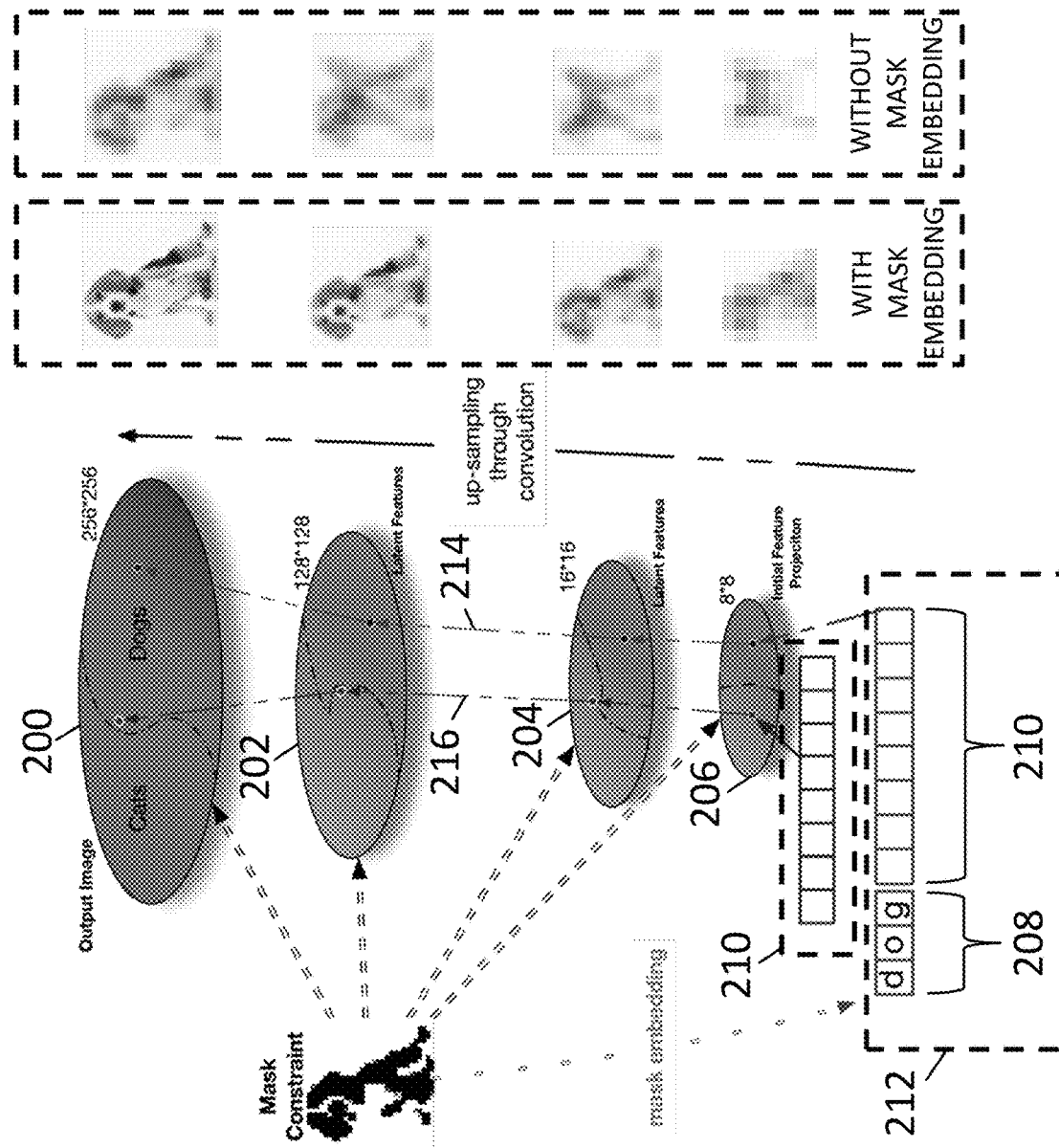
FIG. 2 is a diagram illustrating two image synthesis models including one with mask embedding at an initial projection layer and another without mask embedding.

FIG. 2 is a diagram illustrating aspects of two image synthesis processes including one with mask embedding at an initial projection layer and another without mask embedding. On the left side of FIG. 2, various feature spaces associated with an image generation process and a series of convolution layers are depicted. On the right side of FIG. 2, two example sets of images, one set representing output of an image synthesis process that uses mask embedding and the other set representing output of an image synthesis process that does not use mask embedding. For simplicity, latent features are depicted as low resolution images in FIG. 2. At inference time, an example model with mask embedding can project base features onto a correct manifold using combined input 212 comprising mask embedding input 208 and a latent features vector 210 and can perform proper up-sampling through convolution layers. However, an example model without mask embedding can project only an average base image using latent features vector 210 and can inefficiently map the average base image to a dog to comply with the mask constraint.

Figure 3:
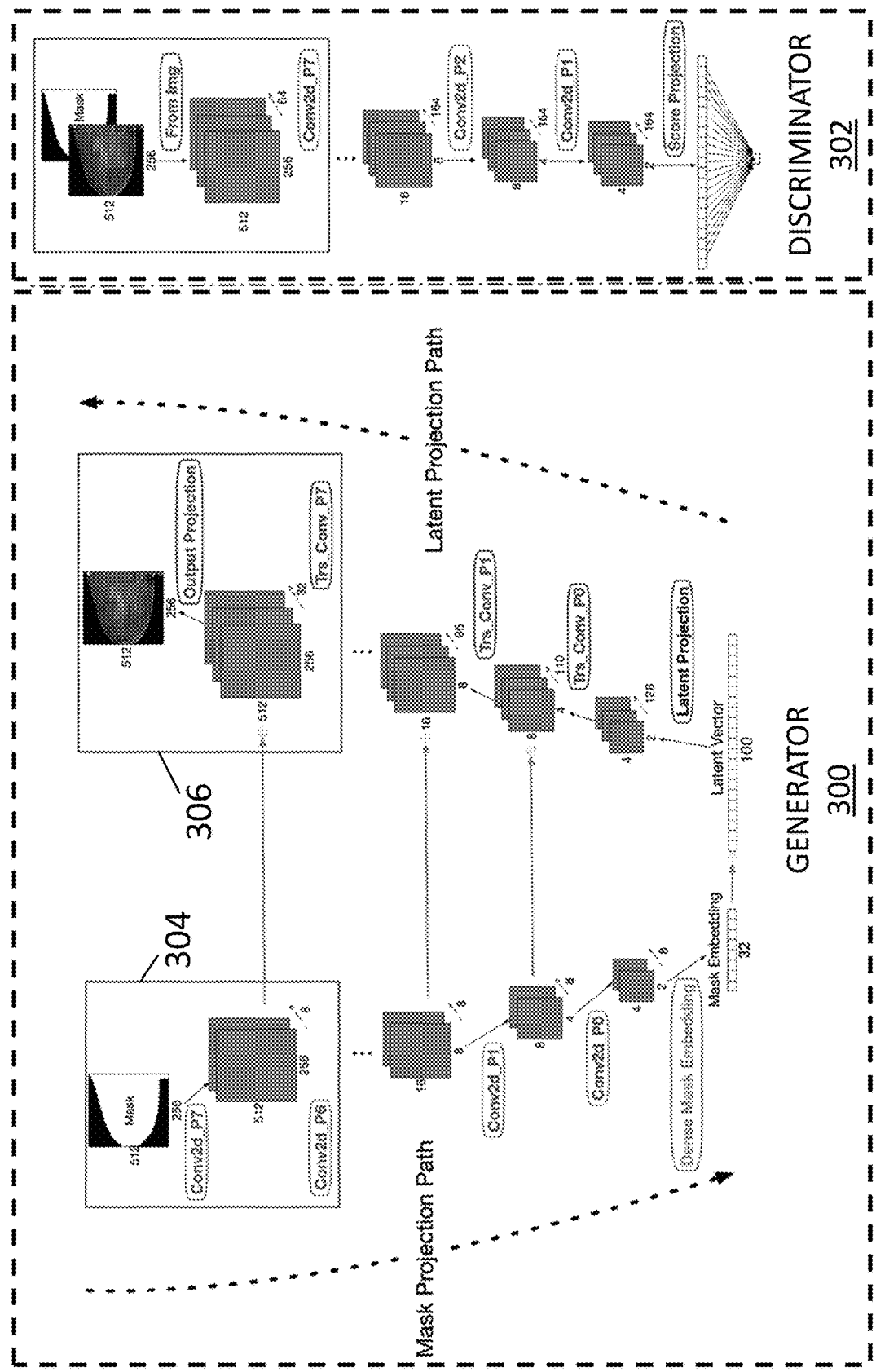
FIG. 3 is a diagram illustrating an example generator and discriminator of a conditional generative adversarial network (cGAN) usable for realistic high-resolution image synthesis.

Referring to FIG. 2, Ellipse 200 represents two partitions of dog and cat images. Ellipses 202-206 represent various low resolution feature sets or partitions associated with the cat and dog images. Connected by a series of convolution layers, which is a local operation with limited receptive field, each partition is inherited hierarchically and admits similar geometry within each manifold. The image synthesis process with mask embedding represented in FIG. 2 may sample a mask constraint point in a lowest resolution manifold, e.g., by locating a correct partition via mask embedding input 208 and sampling a point within that partition via a latent features vector 210. The image synthesis process represented in FIG. 2 may then use an up-sampling procedure for refining the details and enhancing the mask constraint using vertical injection of mask information as depicted in FIG. 3. In some embodiments, notable differences between our model (e.g., as represented in FIGS. 2 and 3) and other models may include mask embedding input 208 and a latent features vector 210.

Without latent features vector, a model (e.g., Pix2Pix or Pix2Pix-HD) with only mask input does not have sufficient randomness. Hence, the generated image by such a model is nearly uniquely identified by the mask. As such, the diversity of generated images via models without a latent features vector is very limited. In contrast, models described herein (e.g., with and without mask embedding) that use a latent features vector can encode a large diversity of details. As such, a mask embedding model as described herein may generate dramatically different images while still containing fine details.

Without mask embedding, a model (e.g., Tub-GAN) may utilize a constraint that is less emphasized in the lower dimensional features. Further, in such a model, parameters in the later layers potentially have to correct incorrect low resolution image, which limits the capability in expressing details. In contrast, a mask embedding model as described herein potentially finds the correct partition and generates correct latent space representation. Hence, in the mask embedding model, subsequent layers can focus more on generating details.

In FIG. 2, dash line 214 indicates progression of an image synthesis process that uses mask embedding to generate a dog image at different resolutions. Whereas dash line 216 indicates progression of an image synthesis process without mask embedding. Without mask embedding, the image synthesis process generates a low resolution cat image in the beginning due to the lack of mask information. During the later layers, convolution together with mask injection correct the image from cat to dog. However, the final image looks like a dog but is of much lower quality than the final output of the image synthesis process that uses mask embedding. Images in FIG. 2 are not generated by models, but we do observe similar behavior in reality. These observations indicate that incorporating mask embedding input significantly improves the features projection efficiency.

Architecture

FIG. 3 is a diagram illustrating an example generator 300 and an example discriminator 302 of a cGAN usable for realistic high-resolution image synthesis. A notable concept is to perform mask embedding in generator 300 before the latent feature projection layer to increase the overall feature projection efficiency. Generator 300 follows a U-Net style design that can be divided into the mask projection path and the latent projection path. Discriminator 302 takes the output of generator 300 as well as a corresponding mask and produces a probability score.

In some embodiments, when doubling the dimension of the networks at the beginning of each training phase, layers at some positions indicated by boxes 304 and 306 are newly initialized and faded in as described in the progressive training strategy for GAN [9].

In some embodiments, e.g., for a baseline model without mask embedding, the dense mask embedding layer in the generator is removed. In such embodiments, a latent features vector size used by such a model may be adjusted (e.g., from 100 dimensions to 132 dimensions) to maintain the same number of parameters in the latent projection path for a fair performance comparison to a mask embedding model.

In some embodiments, the input of the generator's mask projection path is a 256×512 mask (a binary image in our case). This mask projection path may have 7 convolution layers each with a stride of 2 and a depth of 8 features. The output of the mask projection path may be a 32-dimensional vector (mask embedding) and may be injected into the latent features vector as the input of the latent projection layer. The latent features vector may be a 100-dimensional vector thus the input of the latent projection path may be a 132-dimensional vector. Each mask projection feature block (except for the last one) may then be concatenated onto the corresponding latent projection feature block to complete the U-Net structure. The initial latent feature block may be produced by a dense layer followed by 7 deconvolution layers with a stride of 2 and a size of 4. The number of kernels of each deconvolution layer may start at 128 and decrease by a factor of 0.8 (rounded to the nearest integer) in each following layer. The output of the projection layer may be the synthesized image.

In some embodiments, the input to the mask projection path is a binary edge map. In such embodiments, the mask may undergo a series of blocks, each block consisting of 2 convolution layers with strides of 1 and 2, respectively. Each of these blocks may output an increasing number of features to the following layer and may concatenate only a subset of features (e.g., the first eight features) to the latent projection path to form the mask constraint.

In some embodiments, the mask projection path may include two notable functions. First, the mask projection path may provide spatial constraint for the feature up-sampling process on the latent projection path. Second, the mask projection path may output the mask embedding that informs the latent projection layer the feature clusters that are most likely coherent with the particular mask. In such embodiments, to reflect the fact that mask features from the left contracting path serves mainly as a constraint, eight mask features are concatenated to the expanding path of the network. This design is based on two reasons: more mask features would require additional capacity/parameters to properly merge them into projected latent features (thus increase training difficulty) and the examples presented herein indicate a trained model mostly projects mask features that are almost identical patterns merely in different numerical values.

EXAMPLES

Two examples are discussed below. A first example includes an implementation of a trained medical image synthesis system as described herein for generating realistic high-resolution mammographs using mask information indicating breast shape and a second example includes an implementation of a trained facial image synthesis system as described herein for generating realistic high-resolution facial images using mask information indicating facial features and/or facial expressions.

Medical Image Synthesis Example

Mammography Dataset

For the medical image synthesis example, a mammography dataset collected from our institution was used. The dataset contains 39,778 negative screening subjects. Each exam has at least 4 images (Craniocaudal view and Mediolateral oblique view for each side of the breast), resulting in 443,556 images in total. The pixel values are truncated and normalized to [0,1] using the window level settings provided by the DICOM header. Each image was padded and resized to 256×512. For each mammography image a binary skin mask is generated using Ostu thresholding, where 1 denotes breast region and 0 denotes background. For comparison against the Pix2Pix model [8], we extracted the edge map of each mammography images using Sobel filters in both horizontal and vertical directions and then overlaid the texture map with the corresponding skin mask.

Training

We used the progressive training strategy for GAN [9]. The training was divided into 7 phases. In each phase we doubled the network dimensions and gradually faded in the newly added layer. The model was grown from the resolution of 4×8 to 256×512. We stopped at this resolution due to hardware considerations. We adjusted the batch size and learning rate for each phase so that the standard WGAN-GP [5] converging mechanism was achieved. We trained our model on three 1080 Ti for approximately a week to reach the maximum resolution. For each phase we trained the network until the discriminator loss converged and no further observable improvement was made on the synthesized images.

Results

Figure 5:
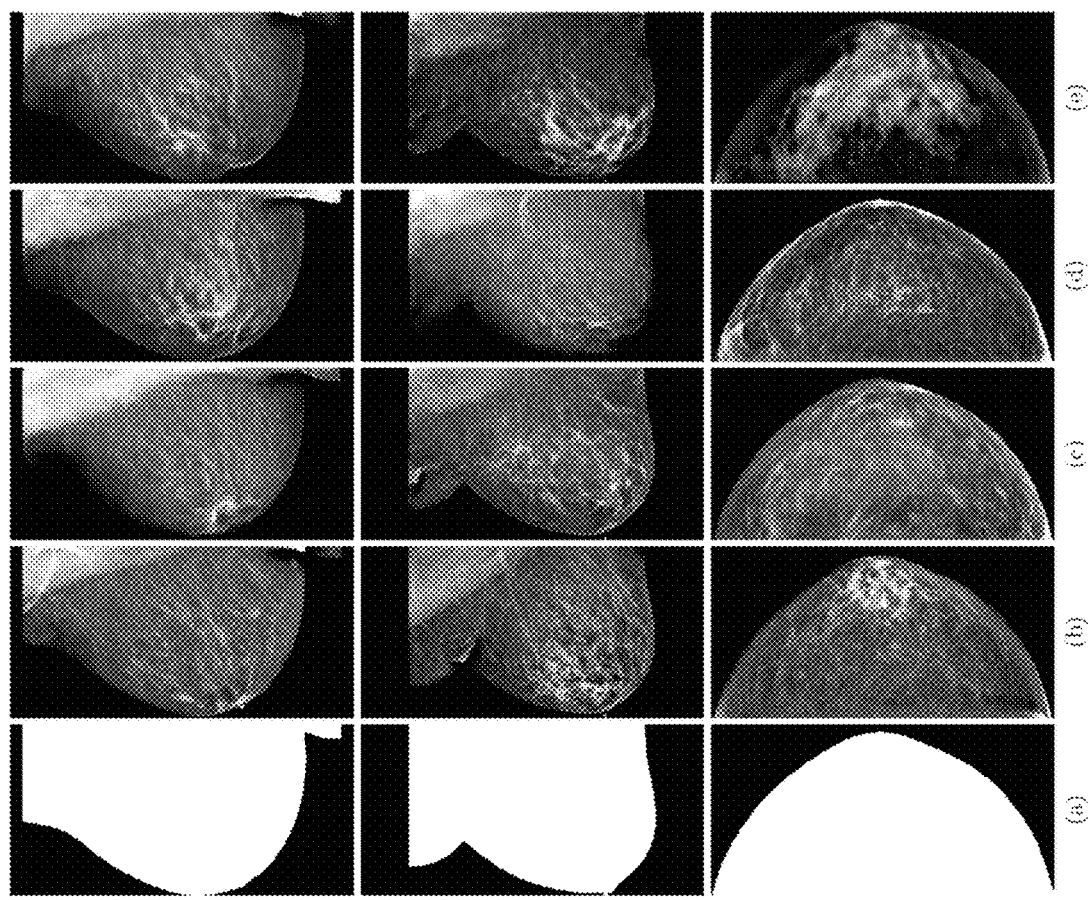
FIG. 5 illustrates different mammograms outputted by an example image synthesis model using various mask constraints and various latent features vectors.

FIG. 5 illustrates different mammograms outputted by an example image synthesis model using various mask constraints and various latent features vectors. In FIG. 5, column (a) shows mask input, column (b) shows original mammograms, and columns (c)-(e) show synthesized mammograms using an image synthesis implementation with mask embedding as described herein. As shown in FIG. 5, synthesized mammograms are depicted using randomly sampled skin masks and latent features vectors.

Figure 6:
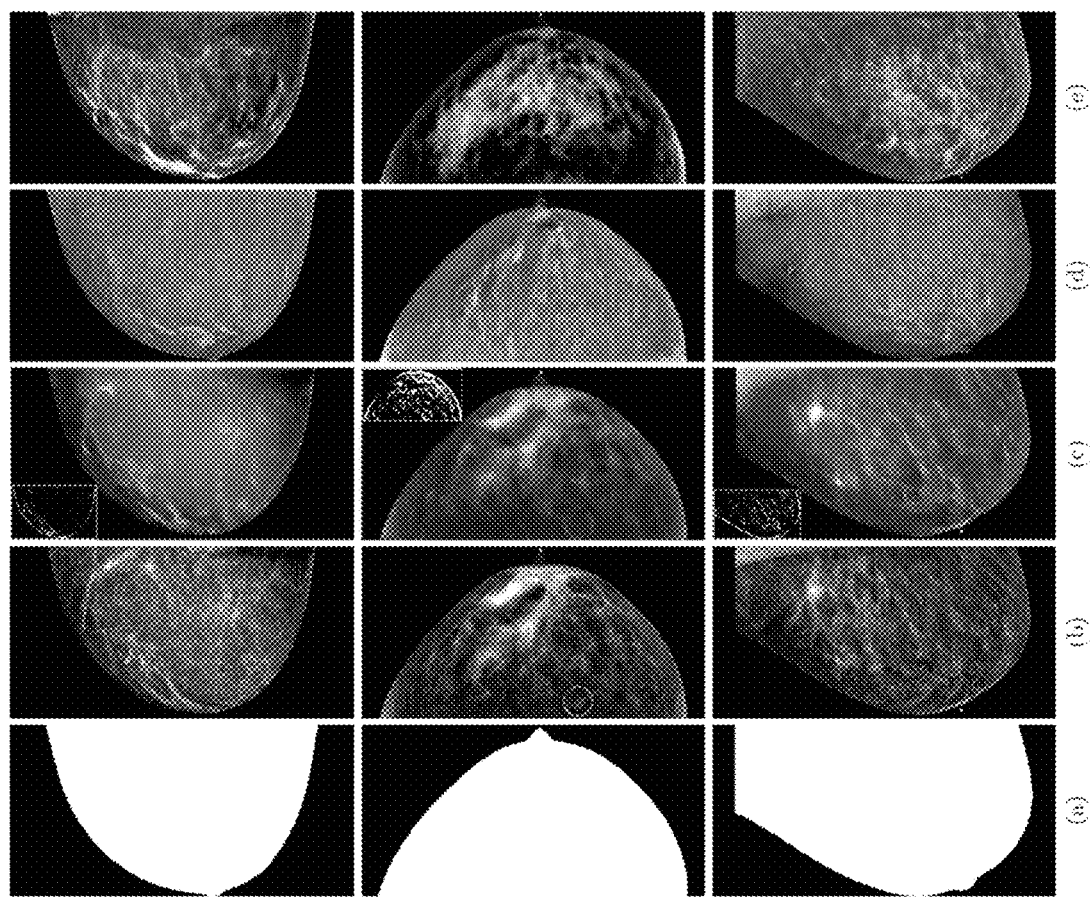
FIG. 6 illustrates different mammograms outputted by different image synthesis models using various mask constraints and various latent features vectors.

FIG. 6 illustrates different mammograms outputted by different image synthesis models using various mask constraints and various latent features vectors. In FIG. 6, column (a) shows mask input, column (b) shows original mammograms, column (c) shows synthesized mammograms using Pix2Pix; column (d) shows synthesized mammograms using an image synthesis implementation without mask embedding as described herein; and column (e) shows synthesized mammograms using an image synthesis implementation with mask embedding as described herein. As shown In FIG. 6, our implemented mask embedding model generates mammograms with much more realistic texture details than other models.

Comparison to Pix2Pix Method

We compared the results of our approach with the well-known Pix2Pix image translation model that takes only semantic mask as input. Results are shown in column (c). Due to the image transformation nature of this model, our first approach using a smooth skin mask as the only input failed to generate any meaningful texture details. In order to evaluate the response of Pix2Pix model to perturbation of mask input, we constructed the texture map as mentioned above in the mammography dataset section. Even trained on masks with the prior information of high frequency tissue structures, the standard Pix2Pix model still under performs our proposed model in terms of fine-grained texture details and variety of parenchymal patterns generated. The Pix2Pix result lacks stochasticity in which a very limited mapping between mask input space and sample space is possible, thus limiting the output variation. Moreover, the same problem limits training stability since the model is forced to map similar input binary patterns with drastically different realization of tissue structures without having the proper mechanism.

Comparison to Baseline Method

We explored the effect of a mask embedding mechanism by removing the mask embedding layer from our proposed model and training this baseline model from scratch. The design of our baseline model is similar to Tub-GAN [19]. The latent input vector is adjusted to be 100+32 so that the total number of parameters in the latent projection layer stays the same to our proposed mask embedding model. The exact same training schedule for our proposed model is repeated. The results are shown in column (d). The generated images have more high-resolution details compared to the Pix2Pix model but lack parenchyma complexity and usually contain obvious artifacts formed during up-sampling. This is an indication of model losing capacity due to the constraint posed by the mask input. A larger collection of comparison images can be found in supplementary material.

Evaluation

For natural image generation there have been several objective metrics to measure the performance of the generative models, such as Inception Score [17], Mode Score [2], and Fréchet Inception Distance [7]. However, in medical image generation, there is no such metric available. Thus, we design a reader study and let expert radiologists assess the realism and quality of the synthesized results.

We randomly picked 50 real breast masks and generated mammograms using the three different approaches: Pix2Pix, our approach without mask embedding, and our approach using mask embedding. All images are presented to readers in random order. Two expert radiologists were asked to rate each mammogram using 5 scores (5: definitely realistic, 4: realistic, 3: neutral, 2: fake, 1: definitely fake). The average scores for real mammograms, synthesized results using Pix2Pix, synthesized results using our approach without mask embedding, and with mask embedding are 3.78, 1.08, 1.34, 2.38, respectively. Although subjective, these numerical results confirm that our approach, particularly with mask embedding, provides a considerable improvement in realism.

Facial Image Synthesis Example

CELEBA-HQ (Face) Dataset

For the facial image synthesis example, the CELEBA-HQ dataset originally compiled by [37], later cleanup and augmented by [9] was used. We extracted 68 face landmarks for each face images in CELEBA-HQ dataset using the Dlib Python Library [38]. The detection is performed at resolution of $1024^2$. We then constructed the face edge map simply by connecting the detected dots from each face landmark. Landmark detections significantly different from the original specified attributes [37] were removed. In total 27000 images were compiled as training images.

Training

For the facial image synthesis experiment, three image synthesis models (Pix2Pix, our implementation without mask embedding, and our implementation with mask embedding) were trained using the WGAN-GP loss formulation [5]. The Pix2Pix model was trained directly at target resolution for 25 epochs. Each of our proposed models (with and without mask embedding) was trained using the progressive growing strategy from the pGAN study [9]. The training started from an output resolution of $8^2$, trained for 45 thousand steps, and then faded in new convolution blocks that doubled the input and output resolution. Given the light-weightiness of the mask projection path, no fading connection is implemented.

To compare the effectiveness of a mask embedding mechanism, the training schedule including batch size, learning rate and number of discriminator optimization per generator in this experiment was kept the same for our proposed models. In particular, a batch size of 256 at the output resolution of 8×8 were used and the batch size was halved every time when doubling output resolution. The learning rate was initially set to constant at 0.001 and increased to 0.002 when the model reached the output resolution of 256. A TensorFlow platform was used in our experiment and each model was trained on 4 NVIDIA V100 for 2 days to reach the final resolution of $512^2$.

Results

We evaluated the effectiveness of our mask embedding model using the sliced Wasserstein distance (SWD) metric [39], following the parameter settings used previously [9]. Due to memory limitation, SWD was averaged over batches of real and synthesized images pairs. We first computed the SWD of 720 image pairs and then repeated until we cover 8192 pairs. We generated the Laplacian pyramid of the images from $512^2$ to the minimal resolution of $16^2$. At each level of the pyramid, 128 patches of size 7×7 were extracted and normalized and the average SWD for each level with respect the real images were computed.

FIG. 4 depicts a table contains SWD values measured between the generated images of different image synthesis models (Pix2Pix, our implementation without mask embedding, and our implementation with mask embedding) to training images. Each table column is one level on the Laplacian pyramid. The SWD metric captures the performance difference of our baseline and proposed models, as well as the Pix2Pix model. From our results, we can infer that using mask embedding is superior and improves the quality of synthesized images, which is also consistent with the visual observations.

Qualitative Comparison

Figure 7:
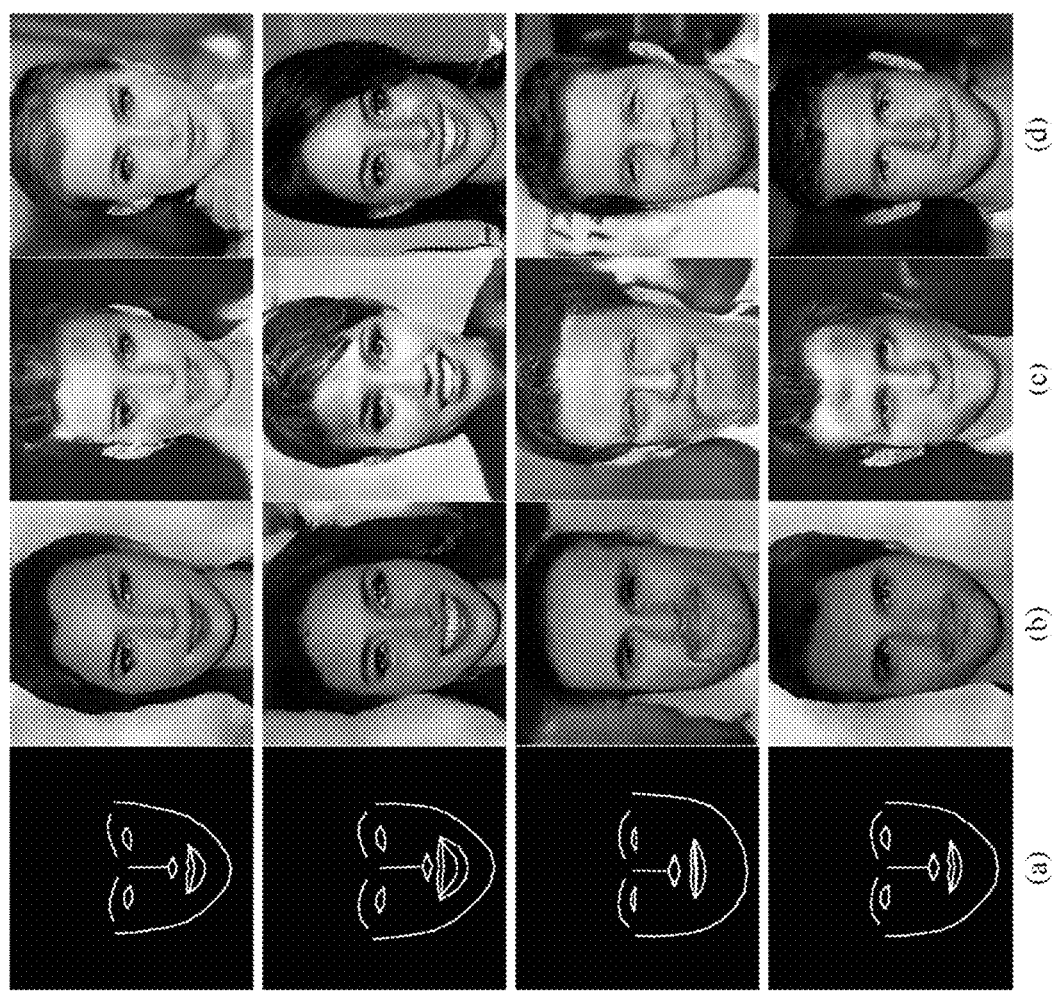
FIG. 7 illustrates different facial images outputted by different image synthesis models using various mask constraints.

FIG. 7 illustrates different facial images outputted by different image synthesis models using various mask constraints. In FIG. 7, column (a) shows mask input, column (b) shows synthesized faces using Pix2Pix; column (c) shows synthesized faces using an image synthesis implementation without mask embedding as described herein; and column (d) shows synthesized faces using an image synthesis implementation with mask embedding as described herein.

FIG. 7 illustrates synthesized results of a mask embedding model (column (d)) and two other models (columns (b) and (c)) using the same latent features vector. Compared to our proposed model (column (d)), the Pix2Pix model (column (b)) is limited to generating coarse images in a similar style. For example, a particular model iteration during training of the Pix2Pix model may generate only black or dark brown hair color, or the skin texture may have a waxy appearance. In this Pix2Pix model, it is likely that the color and texture of faces are decoupled from the mask input, forcing the model to learn only the 'average' face in the dataset, thereby preventing the model from synthesizing realistic, fine-grained textures.

As shown in FIG. 7, the model without embedding (column (c)) also failed to generate high fidelity textures. The generated images in column (c) contain major noise realization and up-sampling artifacts that are indications of reduction in model capacity. This observation fits our hypothesis that the model without mask embedding is forced to project features onto space at the intersection of sample distributions, resulting in blurred texture patterns and ambiguous structures. As a consequence of insufficient generator capacity during training, the model without embedding also generates significantly more artifacts such as diagonal straight lines and checkerboard texture patterns.

5.4 Changing Latent Input

Figure 8:
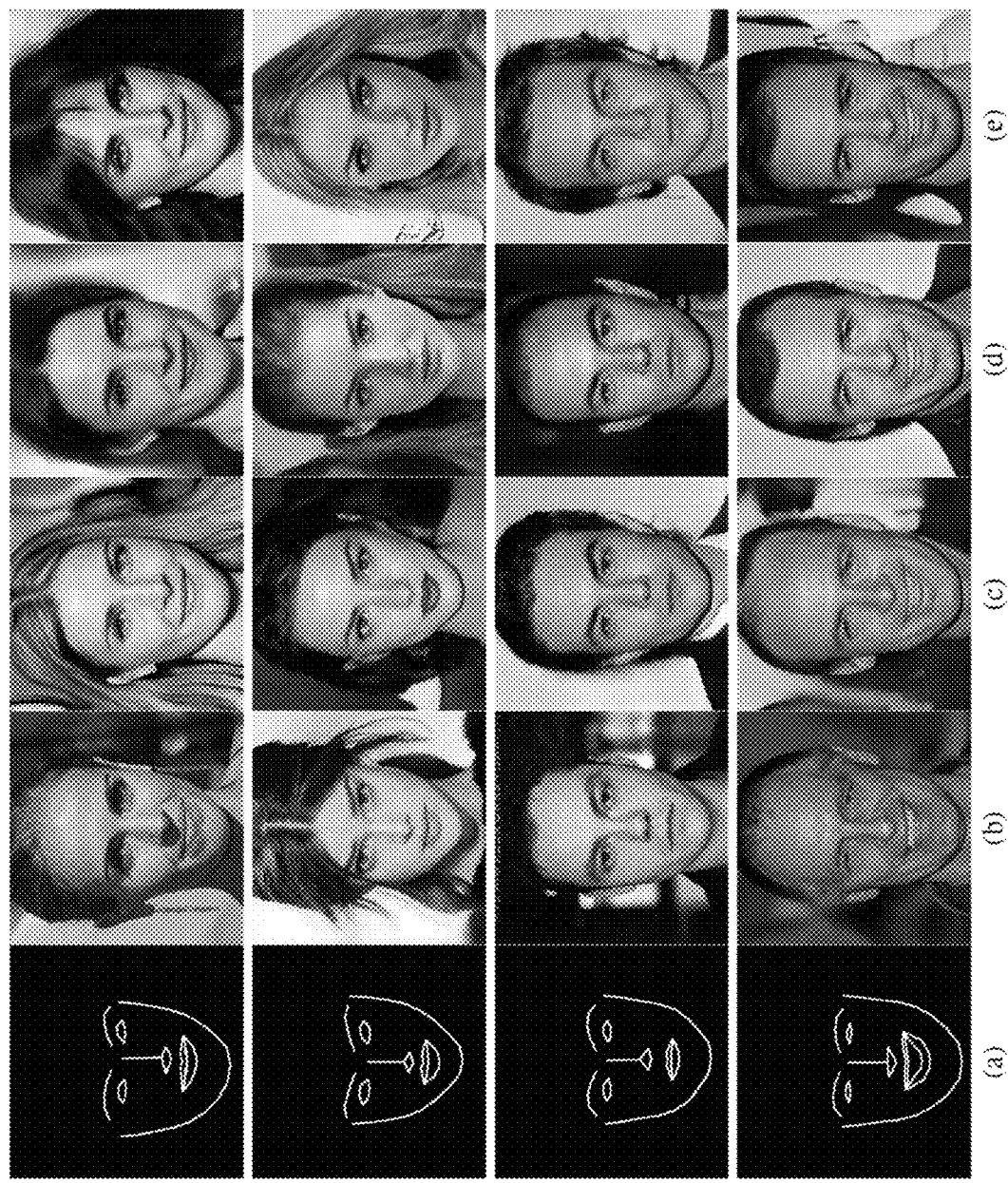
FIG. 8 illustrates different facial images outputted by different image synthesis models using various mask constraints and various latent features vectors.

FIG. 8 illustrates different facial images outputted by different image synthesis models using various mask constraints and various latent features vectors. In FIG. 8, column (a) shows mask input, column (b) shows original faces, column (c) shows synthesized faces using Pix2Pix; column (d) shows synthesized faces using an image synthesis implementation without mask embedding as described herein; and column (e) shows synthesized faces using an image synthesis implementation with mask embedding as described herein.

As shown in FIG. 8, the same mask input can be coupled with different latent features vectors to form different faces. We note however that the latent features vector and mask embedding were not completely disentangled. The latent features vector is responsible more for the style of images, namely the hair style, skin color, facial hair, etc. On the other hand, the face landmarks are as expected determined by the provided mask. We observe some masks are coupled with specific characteristics such as gender and skin color that not necessarily obvious to a human observer when given a binary mask. Such masks may prevent or hinder the latent features vector gaining control for better sample space mapping. In some embodiments, these mask related issues may be alleviated or mitigated by using more abstract mask input together with a larger dataset. Moreover, implementing random blurring and mask feature drop output may increase the output variety as well.

Further Aspects

The subject matter described herein includes systems and/or related processes that utilize binary mask constraint information to guide image synthesis while preserving output variety and realistic, fine-grained texture details. One challenge explored herein was to compensate for the generator capacity reduction caused by the pixel-level mask constraint. An approach described herein utilizes mask embedding to further guide the initial projection of latent features to increase the probability that latent features fall within the manifold constrained by the mask. Such an approach enables the semantic control of the synthesized images while ensuring the fine-grained texture details are looking realistic. This technique may be applied to other high-resolution medical image modalities as well as natural images.

The subject matter described herein includes results from implementations of various image synthesis systems (e.g., processes and/or algorithms) described herein. These results indicate that mask embedding (e.g., an initial projection layer) can significantly impact high-resolution realistic image synthesis. In particular, quantitative and qualitative evaluations validate the effectiveness of a mask embedding mechanism as described herein. The examples described herein are based on semantic input, and the same or similar concepts can be applied to other conditional input, such as textures and text.

Figure 9:
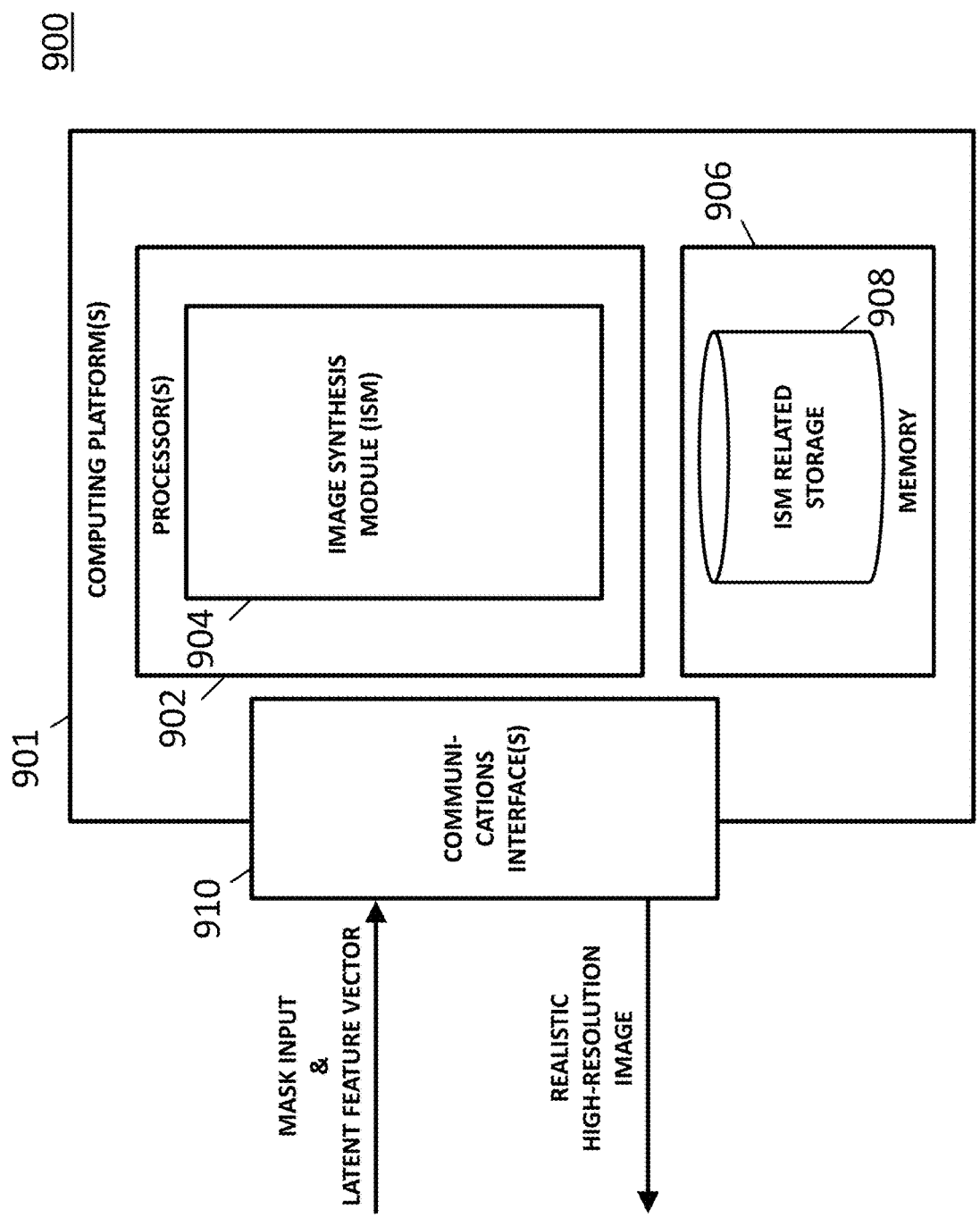
FIG. 9 is a diagram illustrating an example system for realistic high-resolution image synthesis.

FIG. 9 is a diagram illustrating an example image synthesis system (ISS) 900 for realistic high-resolution image synthesis. ISS 900 may include any suitable entity (e.g., a mobile device, a computer, or multiple servers) configurable for generating realistic, high-resolution images (e.g., medical images) using a trained machine learning based model or algorithm, also referred to herein as an image synthesis algorithm or model, where the trained machine learning based model or algorithm includes at least one machine learning algorithm (e.g., a cGAN, a GAN, or another adversarial network) and can use as input a mask embedding vector and a latent features vector. In some embodiments, ISS 900 may include hardware (e.g., a memory and at least one processor) for executing a module (e.g., an application or software) that utilizes mask embedding for performs realistic high-resolution image synthesis.

Referring to FIG. 9, ISS 900 may include one or more computing platform(s) 901. Computing platform(s) 901 may include processor(s) 902. Processor(s) 902 may represent any suitable entity or entities (e.g., one or more hardware-based processors) for processing information and executing instructions or operations. Each of processor(s) 902 may be any type of processor, such as a central processor unit (CPU), a microprocessor, a multi-core processor, and the like.

Computing platform(s) 901 may further include a memory 906 for storing information and instructions to be executed by processor(s) 902. In some embodiments, memory 906 can comprise one or more of random access memory (RAM), read only memory (ROM), static storage such as a magnetic or optical disk, or any other type of machine or non-transitory computer-readable medium.

Computing platform(s) 901 may further include one or more communications interface(s) 910, such as a network interface card or a communications device, configured to provide communications access to various entities (e.g., network-connected devices). In some embodiments, one or more communications interface(s) 910 may be a user interface configured for allowing user (e.g., an operator) to interact with computing platform(s) 901 or related entities. For example, a user interface may include a graphical user interface (GUI) for providing training datasets and various configuration settings for training and/or usage. In some embodiments, memory 906 may be utilized to store an image synthesis module (ISM) 904, or software therein, and an ISM related storage 908.

ISM 904 may be any suitable entity (e.g., software executing on one or more processors) for performing one or more aspects associated with image synthesis. In some embodiments, ISM 904 may be configured for mask embedding for realistic high-resolution image synthesis. For example, ISM 904 may be a trained machine learning based algorithm configured for utilizing mask embedding and latent features vectors for generating realistic high-resolution medical images. In this example, ISM 904 may be configured for receiving, as input, a mask embedding vector and a latent features vector, wherein the mask embedding vector acts as a semantic constraint; generating, using a trained image synthesis algorithm and the input, a realistic image, wherein the realistic image is constrained by the mask embedding vector; and outputting, by the trained image synthesis algorithm, the realistic image to a display or a storage device.

In some embodiments, ISM 904 may determine and/or provide images and/or related information to one or more entities, such as a user, a system operator, a medical records system, a healthcare provider, or any combination thereof.

Memory 906 may be any suitable entity or entities (e.g., non-transitory computer readable media) for storing various information. Memory 906 may include an ISM related storage 908. ISM related storage 908 may be any suitable entity (e.g., a database embodied or stored in computer readable media) usable for storing synthesized images, real or original images, training datasets, machine learning algorithms and/or models, metrics and testing information, and/or predetermined information or settings for ISS 900 or ISM 904. For example, ISM related storage 908 may include user preferences and/or historical data when training or executing ISM 904.

In some embodiments, ISM related storage 908 may be accessible by ISM 904 and/or other modules of computing platform(s) 901 and may be located externally to or integrated with ISM 904 and/or computing platform(s) 901. For example, ISM related storage 908 may be stored at a server located remotely from ISM 904 but still accessible by ISM 904. In another example, ISM related storage 908 may be distributed or separated across multiple nodes.

In some embodiments, users may interact with ISS 900 through a number of ways, such as via one or more networks. In such embodiments, one or more servers accessible through the network(s) can host ISS 900. The one or more servers can also contain or have access to the one or more data stores for storing data for ISS 900, or receive input data (e.g., masks or related mask embedding vectors and/or training images) from external sources. It should be appreciated that in some embodiments ISS 900 or a related server may be self-contained and not connected to external networks due to security or other concerns.

It will be appreciated that the above described modules in FIG. 9 are for illustrative purposes and that features or portions of features described herein may be performed by different and/or additional modules, components, or nodes. For example, aspects of image synthesis described herein may be performed by ISM 904, computing platform(s) 901, and/or other modules or nodes. Further, it will be understood that while various machine learning algorithms are discussed above, other known machine learning algorithms may also be used in realistic high-resolution image synthesis.

Figure 10:
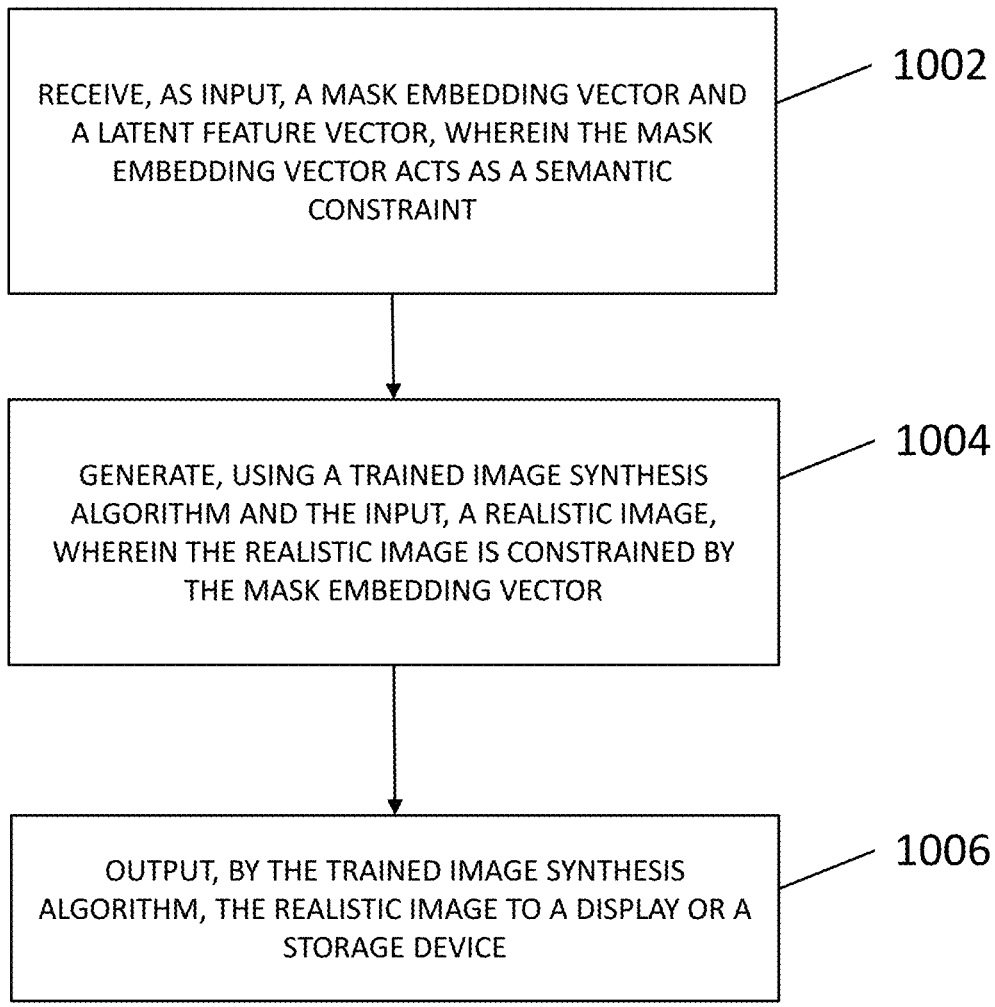
FIG. 10 is a diagram illustrating an example process for realistic high-resolution image synthesis.

FIG. 10 is a diagram illustrating an example process 1000 for realistic high-resolution image synthesis. In some embodiments, process 1000 described herein, or portions thereof, may be performed at or by ISS 900, computing platform(s) 901, ISM 904, and/or another module or node. For example, ISS 900 or computing platform(s) 901 may be a mobile device, a computer, or other equipment (e.g., a medical device) and ISM 904 may include or provide an application running or executing on computing platform(s) 901. In some embodiments, process 1000 may include steps 1002-1006.

In step 1002, a mask embedding vector and a latent features vector may be received as input. In some embodiments, the mask embedding vector may act as a semantic constraint.

In step 1004, a realistic image may be generated using a trained image synthesis algorithm and the input. In some embodiments, the realistic image may be constrained by the mask embedding vector.

In step 1006, the realistic image may be outputted to a display or a storage device by the trained image synthesis algorithm.

In some embodiments, the trained image synthesis algorithm may include or use a generative adversarial network.

In some embodiments, a generative adversarial network may be trained using a generator for generating realistic images and a discriminator for determining whether generated images are realistic, wherein, during training, output from the generator is provided to the discriminator and output from the discriminator is used by the generator to improve its ability to generate realistic image.

In some embodiments, a generator may include a mask projection path for generating a mask embedding vector and a latent projection path for generating a latent features vector.

In some embodiments, during a training phase, a discriminator may take as input an image outputted by a generator and mask input used by the generator to generate the input. In such embodiments, during the training phase, the discriminator may produce a probability score indicating the likelihood that the image outputted by the generator is realistic.

In some embodiments, the trained image synthesis algorithm may use a single vector that is derived by combining a mask embedding vector and a latent features vector.

In some embodiments, a realistic image generated by the trained image synthesis algorithm may include a medical image, a mammogram, an X-ray, a radiography image, an ultrasound, a computed tomography (CT) image, a nuclear medicine including positron emission tomography (PET) image, a magnetic resonance imaging (MRI) image, or a natural image (e.g., an image of a human face or an image of nature).

In some embodiments, ISS 900 and/or computing platform(s) 901 for implementing process 1000 may include a mobile device, a smartphone, a tablet computer, a laptop computer, a computer, a server, or a medical device.

It will be appreciated that process 1000 is for illustrative purposes and that different and/or additional actions may be used. It will also be appreciated that various actions described herein may occur in a different order or sequence.

It should be noted that ISS 900, computing platform(s) 901, ISM 904, and/or functionality described herein may constitute a special purpose computing device. Further, ISS 900, computing platform(s) 901, ISM 904, and/or functionality described herein can improve the technological field of image synthesis by providing machine learning mechanisms that utilize mask embedding and latent features vectors. For example, during training, ISM 904 may utilize mask input and a latent features vector to identify a number of a related images in a domain space based on the input during an initial projection layer and may use subsequent layers to improve and/or synthesis fine grain details (based on the related images), where the output image is constrained by the mask input.

The disclosure of each of the following references is incorporated herein by reference in its entirety to the extent not inconsistent herewith and to the extent that it supplements, explains, provides a background for, or teaches methods, techniques, and/or systems employed herein.

REFERENCES

[1] Arjovsky, M., Chintala, S., Bottou, L.: Wasserstein generative adversarial networks. In: Precup, D., Teh, Y. W. (eds.) Proceedings of the 34th International Conference on Machine Learning. vol. 70, pp. 214-223 (2017).

[2] Che, T., Li, Y., Jacob, A. P., Bengio, Y., Li, W.: Mode regularized generative adversarial networks. CoRR abs/1612.02136 (2016).

[3] Costa, P., Galdran, A., Meyer, M. I., Niemeijer, M., Abrmoff, M., Mendona, A. M., Campilho, A.: End-to-end adversarial retinal image synthesis. IEEE Transactions on Medical Imaging 37(3), 781-791 (March 2018).

[4] Goodfellow, I., Pouget-Abadie, J., Mirza, M., Xu, B., Warde-Farley, D., Ozair, S., Courville, A., Bengio, Y.:

Generative adversarial nets. In: Ghahramani, Z., Welling, M., Cortes, C., Lawrence, N. D., Weinberger, K. Q. (eds.) Advances in Neural Information Processing Systems 27, pp. 2672-2680 (2014).

[5] Gulrajani, I., Ahmed, F., Arjovsky, M., Dumoulin, V., Courville, A. C.: Improved training of wasserstein gans. In: Guyon, I., Luxburg, U. V., Bengio, S., Wallach, H., Fergus, R., Vishwanathan, S., Garnett, R. (eds.) Advances in Neural Information Processing Systems, pp. 5767-5777 (2017).

[6] Han, C., Hayashi, H., Rundo, L., Araki, R., Shimoda, W., Muramatsu, S., Furukawa, Y., Mauri, G., Nakayama, H.: Gan-based synthetic brain mr image generation. In: 2018 IEEE 15th International Symposium on Biomedical Imaging (ISBI 2018). pp. 734-738 (April 2018). https://doi.org/10.1109/ISBI.2018.8363678

[7] Heusel, M., Ramsauer, H., Unterthiner, T., Nessler, B., Klambauer, G., Hochreiter, S.: Gans trained by a two time-scale update rule converge to a nash equilibrium. CoRR abs/1706.08500 (2017).

[8] Isola, P., Zhu, J. Y., Zhou, T., Efros, A. A.: Image-to-image translation with conditional adversarial networks. In: The IEEE Conference on Computer Vision and Pattern Recognition (CVPR) (July 2017).

[9] Karras, T., Aila, T., Laine, S., Lehtinen, J.: Progressive growing of gans for improved quality, stability, and variation. CoRR abs/1710.10196 (2017)

[10] Karras, T., Laine, S., Aila, T.: A style-based generator architecture for generative adversarial networks. CoRR abs/1812.04948 (2018).

[11] Korkinof, D., Rijken, T., O'Neill, M., Yearsley, J., Harvey, H., Glocker, B.: High-resolution mammogram synthesis using progressive generative adversarial networks. CoRR abs/1807.03401 (2018).

[12] Mirza, M., Osindero, S.: Conditional Generative Adversarial Nets. arXiv e-prints arXiv:1411.1784 (November 2014).

[13] Moradi, M., Madani, A., Karargyris, A., F. Syeda-Mahmood, T.: Chest x-ray generation and data augmentation for cardiovascular abnormality classification. p. 57 (March 2018).

[14] Nie, D., Trullo, R., Lian, J., Wang, L., Petitjean, C., Ruan, S., Wang, Q., Shen, D.: Medical image synthesis with deep convolutional adversarial networks. IEEE Transactions on Biomedical Engineering 65(12), 2720-2730 (December 2018).

[15] Nie, D., Trullo, R., Lian, J., Petitjean, C., Ruan, S., Wang, Q., Shen, D.: Medical image synthesis with context-aware generative adversarial networks. In: Descoteaux, M., Maier-Hein, L., Franz, A., Jannin, P., Collins, D. L., Duchesne, S. (eds.) Medical Image Computing and Computer-Assisted Intervention MICCAI 2017. pp. 417-425. Springer International Publishing, Cham (2017).

[16] Ronneberger, O., Fischer, P., Brox, T.: U-net: Convolutional networks for biomedical image segmentation. CoRR abs/1505.04597 (2015).

[17] Salimans, T., Goodfellow, I., Zaremba, W., Cheung, V., Radford, A., Chen, X., Chen, X.: Improved techniques for training gans. In: Lee, D. D., Sugiyama, M., Luxburg, U. V., Guyon, I., Garnett, R. (eds.) Advances in Neural Information Processing Systems 29, pp. 2234-2242 (2016).

[18] Yi, X., Walia, E., Babyn, P.: Generative adversarial network in medical imaging: A review. CoRR abs/1809.07294 (2018).

[19] Zhao, H., Li, H., Maurer-Stroh, S., Cheng, L.: Synthesizing retinal and neuronal images with generative adversarial nets. Medical Image Analysis 49, 14-26 (2018).

[20] Ronneberger, O., Fischer, P., Brox, T.: U-net: Convolutional networks for biomedical image segmentation. MICCAI (2015).

[21] Wang, T., Liu, M., Zhu, J., Tao, A., Kautz, J., Catanzaro, B.: High-resolution image synthesis and semantic manipulation with conditional gans. Proceedings of the IEEE Conference on Computer Vision and Pattern Recognition (2018).

[22] Chen, Q., Koltun, V.: Photographic image synthesis with cascaded refinement networks. IEEE International Conference on Computer Vision, ICCV 2017, Venice, Italy, Oct. 22-29, 2017, pages 1520-1529 (2017).

[23] Zhang, H., Xu, T., Li, H., Zhang, S., Wang, X., Huang, X., Metaxas, D.: Stackgan: Text to photo-realistic image synthesis with stacked generative adversarial networks. ICCV (2017).

[24] Mirza, M., Osindero, S.: Conditional generative adversarial nets. CoRR, abs/1411.1784 (2014).

[25] Gauthier, J.: Conditional generative adversarial nets for convolutional face generation. (2015).

[26] Wang, X., Li, W., Mu, G., Huang, D., Wang, Y.: Facial expression synthesis by u-net conditional generative adversarial networks. Proceedings of the 2018 *ACM on International Conference on Multimedia Retrieval*, ICMR '18, pages 283-290, New York, N.Y., USA, ACM (2018).

[27] Antipov, G., Baccouche, M., Dugelay, J.: Face aging with conditional generative adversarial networks. 2017 IEEE International Conference on Image Processing (ICIP), pages 2089-2093 (September 2017).

[28] N. Bayramoglu, M. Kaakinen, L. Eklund, and J. Heikkilä. Towards virtual h e staining of hyperspectral lung histology images using conditional generative adversarial networks. In 2017 IEEE International Conference on Computer Vision Workshops (ICCVW), pages 64-71 (October 2017).

[29] Rezaei M., Harmuth, K., Gierke, W., Kellermeier, T., Fischer, M., Yang, H., Meinel, C.: A conditional adversarial network for semantic segmentation of brain tumor. Brainlesion: Glioma, Multiple Sclerosis, Stroke and Traumatic Brain Injuries, pages 241-252, Springer International Publishing, Cham (2018).

[30] Dar, S. U., Yurt, M., Karacan, L., Erdem, A., Erdem, E., cukur, T.: Image synthesis in multi-contrast mri with conditional generative adversarial networks. *IEEE Transactions on Medical Imaging*, pages 1-1 (2019).

[31] Liu, X., Meng, G., Xiang, S., Pan, C.: Semantic image synthesis via conditional cycle-generative adversarial networks. 2018 24*th International Conference on Pattern Recognition (ICPR)*, pages 988-993 (August 2018).

[32] Yildirim, G., Seward, C., Bergmann, U.: Disentangling Multiple Conditional Inputs in GANs. arXiv e-prints, page arXiv:1806.07819 (June 2018).

[33] Chen, C., Ross, A.: Matching Thermal to Visible Face Images Using a SemanticGuided Generative Adversarial Network. arXiv e-prints, page arXiv:1903.00963 (March 2019).

[34] Curtó, J., Zarza, I., Torre, F., King, I., Lyu, M.: High-resolution deep convolutional generative adversarial networks, cite arxiv:1711.06491 (2017).

[35] Shaham, T., Dekel, T., Michaeli, T.: SinGAN: Learning a Generative Model from a Single Natural Image. arXiv e-prints, page arXiv:1905.01164 (May 2019).

[36] Antoniou, A., Storkey, A., Edwards, H.: Data augmentation generative adversarial networks (2018).

[37] Liu, Z., Luo, P., Wang, X., Tang, X.: Deep learning face attributes in the wild. Proceedings of International Conference on Computer Vision (ICCV), (December 2015).

[38] King, D.: Dlib-ml: A machine learning toolkit. Journal of Machine Learning Research, 10:1755-1758 (2009).

[39] Julien, R., Peyré, G., Delon, J., Marc, B.: Wasserstein Barycenter and its Application to Texture Mixing. SSVM'11, pages 435-446, Israel, 2011. Springer (2011).

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for realistic high-resolution image synthesis, the method comprising:
at a computing platform:
receiving, as input, a mask embedding vector and a latent features vector, wherein the mask embedding vector acts as a semantic constraint;
generating, using a trained image synthesis algorithm and the input, a realistic image, wherein the realistic image is constrained by the mask embedding vector, wherein the trained image synthesis algorithm uses a single vector derived by combining the mask embedding vector and the latent features vector, wherein the trained image synthesis algorithm includes a generator that includes a mask projection path and a latent projection path, wherein output for the mask projection path includes the mask embedding vector, wherein input for the latent projection path includes the single vector and output for the latent projection path includes the realistic image; and
outputting, by the trained image synthesis algorithm, the realistic image to a display or a storage device.

2. The method of claim 1 wherein the trained image synthesis algorithm includes or uses a generative adversarial network.

3. The method of claim 2 wherein the generative adversarial network is trained using the generator for generating realistic images and a discriminator for determining whether generated images are realistic, wherein, during training, output from the generator is provided to the discriminator and output from the discriminator is used by the generator to improve its ability to generate realistic image.

4. The method of claim 3 wherein, during a training phase, the discriminator takes as input an image outputted by the generator and mask input used by the generator.

5. The method of claim 4 wherein, during the training phase, the discriminator produces a probability score indicating the likelihood that the image outputted by the generator is realistic.

6. The method of claim 1 wherein the realistic image includes a medical image, a mammogram, an X-ray, a radiography image, an ultrasound, a computed tomography (CT) image, a nuclear medicine including positron emission tomography (PET) image, a magnetic resonance imaging (MRI) image, or a natural image.

7. The method of claim 1 wherein the computing platform includes a mobile device, a smartphone, a tablet computer, a laptop computer, a computer, a risk mitigation device, a server, or a medical device.

8. A system for realistic high-resolution image synthesis, the system comprising:
at least one processor;
a memory; and
a computing platform including the at least one processor and memory, wherein the computing platform is configured for:
receiving, as input, a mask embedding vector and a latent features vector, wherein the mask embedding vector acts as a semantic constraint;
generating, using a trained image synthesis algorithm executing on the at least one processor and the input, a realistic image, wherein the realistic image is constrained by the mask embedding vector, wherein the trained image synthesis algorithm uses a single vector derived by combining the mask embedding vector and the latent features vector, wherein the trained image synthesis algorithm includes a generator that includes a mask projection path and a latent projection path, wherein output for the mask projection path includes the mask embedding vector, wherein input for the latent projection path includes the single vector and output for the latent projection path includes the realistic image; and
outputting, by the trained image synthesis algorithm, the realistic image to a display or a storage device.

9. The system of claim 8 wherein the trained image synthesis algorithm includes or uses a generative adversarial network.

10. The system of claim 9 wherein the generative adversarial network is trained using the generator for generating realistic images and a discriminator for determining whether generated images are realistic, wherein, during training, output from the generator is provided to the discriminator and output from the discriminator is used by the generator to improve its ability to generate realistic image.

11. The system of claim 10 wherein, during a training phase, the discriminator takes as input an image outputted by the generator and mask input used by the generator.

12. The system of claim 11 wherein, during the training phase, the discriminator produces a probability score indicating the likelihood that the image outputted by the generator is realistic.

13. The system of claim 8 wherein the realistic image includes a medical image, a mammogram, an X-ray, a radiography image, an ultrasound, a computed tomography (CT) image, a nuclear medicine including positron emission tomography (PET) image, a magnetic resonance imaging (MRI) image, or a natural image.

14. The system of claim 8 wherein the computing platform includes a mobile device, a smartphone, a tablet computer, a laptop computer, a computer, a risk mitigation device, a server, or a medical device.

15. The system of claim 9 wherein input for the mask projection path includes a binary edge mask, a binary skin mask, a binary mask, or a binary image.

16. A non-transitory computer readable medium comprising computer executable instructions that when executed by at least one processor of a computer cause the computer to perform steps comprising:
receiving, as input, a mask embedding vector and a latent features vector, wherein the mask embedding vector acts as a semantic constraint;
generating, using a trained image synthesis algorithm and the input, a realistic image, wherein the realistic image is constrained by the mask embedding vector, wherein the trained image synthesis algorithm uses a single vector derived by combining the mask embedding vector and the latent features vector, wherein the trained image synthesis algorithm includes a generator that includes a mask projection path and a latent projection path, wherein output for the mask projection path includes the mask embedding vector, wherein input for the latent projection path includes the single vector and output for the latent projection path includes the realistic image; and outputting, by the trained image synthesis algorithm, the realistic image to a display or a storage device.

17. The non-transitory computer readable medium of claim 16 wherein the trained image synthesis algorithm includes or uses a generative adversarial network.

* * * * *